United States Patent

Milam et al.

[11] Patent Number: 5,962,757
[45] Date of Patent: Oct. 5, 1999

[54] DEHYDROGENATION CATALYST AND PROCESS

[75] Inventors: Stanley Nemec Milam, Spring; Brent Howard Shanks, Houston, both of Tex.

[73] Assignee: Shell Oil Company, Houston, Tex.

[21] Appl. No.: 08/839,841

[22] Filed: Apr. 17, 1997

Related U.S. Application Data

[60] Continuation of application No. 08/530,505, Sep. 19, 1995, abandoned, which is a division of application No. 08/355,949, Dec. 14, 1994, abandoned.

[51] Int. Cl.⁶ .............................. C07C 2/64; C07C 5/09; B01J 23/58
[52] U.S. Cl. .................. 585/444; 585/379; 585/445; 585/629; 585/630; 585/631; 585/662; 585/663; 502/330; 502/326; 502/331
[58] Field of Search ..................... 585/379, 440, 585/444, 445, 629, 630, 631, 660, 661, 662, 663; 502/330, 326, 331

[56] References Cited

U.S. PATENT DOCUMENTS

| | | | |
|---|---|---|---|
| 3,291,756 | 12/1966 | Bowman | 252/474 |
| 3,870,764 | 3/1975 | Cichowski et al. | 260/680 E |
| 3,993,591 | 11/1976 | Cichowski et al. | 252/432 |
| 4,152,300 | 5/1979 | Riesser | 252/462 |
| 4,565,899 | 1/1986 | Burress | 585/445 |
| 4,684,619 | 8/1987 | Moore | 502/330 |
| 4,804,799 | 2/1989 | Lewis et al. | 585/444 |
| 4,857,498 | 8/1989 | Dejaifve et al. | 502/304 |
| 5,023,225 | 6/1991 | Williams et al. | 502/304 |
| 5,171,914 | 12/1992 | Hamilton, Jr. | 585/444 |
| 5,376,613 | 12/1994 | Dellinger et al. | 502/304 |
| 5,461,179 | 10/1995 | Chen et al. | 585/440 |

FOREIGN PATENT DOCUMENTS

| | | |
|---|---|---|
| 0459424 A1 | 5/1991 | European Pat. Off. . |
| 0514177 A1 | 5/1992 | European Pat. Off. . |
| 2387199 | 12/1978 | France . |

*Primary Examiner*—Glenn Caldarola
*Assistant Examiner*—Thuan D. Dang
*Attorney, Agent, or Firm*—Todd F. Volyn

[57] ABSTRACT

Dehydrogenation catalysts are prepared by a predoping process comprising, mixing iron oxide materials with a predopant to form a blend of iron oxide and predopant and heating the blend to the predoping conditions and thereafter forming a catalyst. The catalysts so prepared are useful in the dehydrogenation of a composition having at least one carbon—carbon double bond. Such catalytic uses include the conversion of ethylbenzene to styrene.

9 Claims, No Drawings

DEHYDROGENATION CATALYST AND PROCESS

This is a continuation of application Ser. No. 08/530,505, filed Sep. 19, 1995, now abandoned which is a division of application Ser. No. 08/355,949, filed Dec. 14, 1994, now abandoned.

FIELD OF THE INVENTION

This invention relates to the dehydrogenation of hydrocarbons and catalysts useful in such processes.

BACKGROUND OF THE INVENTION

Iron oxide based catalysts are widely used in the dehydrogenation of hydrocarbons. Iron oxide materials from which these catalyst may be prepared exist naturally as several minerals. These minerals include red, yellow, brown, and black iron oxide materials. For example, red iron oxide minerals are usually hematite ($\alpha$-$Fe_2O_3$), yellow iron oxide can be lepidocrocite ($\gamma$-FeOOH or $Fe_2O_3.nH_2O$) or goethite ($\alpha$-FeOOH or $Fe_2O_3.nH_2O$), brown iron oxide is maghemite ($\gamma$-$Fe_2O_3$), and black iron oxide is magnetite ($Fe_3O_4$).

Synthetic hematite, goethite, lepidocrocite, maghemite, and magnetite are among the most important iron oxides for use in industrial applications. Synthetic hematite produced by calcination of synthetic goethite is most widely used to catalyze the conversion of ethylbenzene to styrene because these materials often have the highest purity (>98% $Fe_2O_3$).

U.S. Pat. Nos. 4,052,338; 4,098,723; 4,143,083; 4,144,197; and 4,152,300 all propose dehydrogenation catalysts comprising small amounts of oxidic compounds and rare earths added to iron-potassium oxide base catalysts. In each case, these components were blended, pelletized, and dried. The pellets were then calcined. Selectivity was consistent at approximately 92 mole % (for styrene) among these compositions at a 70% molar conversion of ethylbenzene to products. U.S. Pat. No. 5,023,225 proposed a catalyst with improved stability. In this patent, prior to catalyst formation, a yellow iron oxide was heated in the presence of a small amount of a chromium compound until the yellow iron oxide was converted to red iron oxide.

It has now been found that iron oxide based catalysts with enhanced catalytic properties can be prepared by predoping iron oxide compounds under certain conditions. The catalysts produced from such predoped iron oxides display particularly noteworthy selectivity improvements over iron oxide based catalysts which have not been so predoped.

SUMMARY OF THE INVENTION

In one aspect of this invention catalysts are prepared by a predoping process comprising, mixing iron oxide materials with a predopant to form a blend of iron oxide and predopant and heating the blend.

In another aspect of the invention, a process for the dehydrogenation of a composition having at least one carbon—carbon single bond is presented which comprises contacting the composition having the saturated portion with a catalytic quantity of a compostion comprising predoped iron oxide.

In yet another aspect of the invention, predoped iron oxide is used to catalyze the conversion of ethylbenzene to styrene.

DETAILED DESCRIPTION OF THE INVENTION

This invention relates to a process for the preparation of a compound having the general formula: $R_1R_2CCH_2$ (Formula I) wherein $R_1$ and $R_2$ each represent an alkyl, an alkenyl, an aryl (such as a phenyl) group or a hydrogen atom, by the dehydrogenation of a compound having the general formula: $R_1R_2CHCH_3$ (Formula II) wherein $R_1$ and $R_2$ have the same meanings as in Formula I. This process generally involves contacting a compound of Formula II with a catalyst comprising iron oxide in the presence of super-heated steam and elevated temperatures. Ordinarilly, the catalyst is pelletized and comprises between about 50 and about 100 percent by weight, basis $Fe_2O_3$, of a predoped iron oxide.

$R_1$ of Formula II may represent a phenyl group with one or more substituents; particularly methyl groups. Preferably, $R_1$ is an unsubstituted phenyl group and $R_2$ is a hydrogen or a methyl group. Ethylbenzene is a most preferred starting compound from which stryene may be produced. The alkanes of Formula II preferably have in the range of from 2 to about 20 carbon atoms per molecule. Molecules having from about 3 to about 8 carbon atoms such as n-butane and 2-methylbutane are even more preferred. The alkenes of Formula II preferably have in the range of from about 4 to about 20 carbon atoms. Molecules having from about 4 to about 8 carbon atoms such as 1-butene (forming 1,3,-butadiene), 2-methyl-1-butene and 3-methyl-1-butene (both forming isoprene) are even more preferred.

The catalysts of this invention are comprised of predoped iron oxide materials. Preferred iron oxide materials for predoping are comprised of $\alpha$-$Fe_2O_3$. However, the iron oxide materials which may be predoped according to this invention can also comprise hydrated or non-hydrated $Fe_2O_3$ or precursors thereto whether synthetically produced or naturally found. It is most preferred that, as a result of the predoping process, the iron oxide particles used in the catalyst according to this invention are the restructured iron oxide particles described in copending patent application Ser. No. 08/356,024 now abandonded and filed as a continuation application having Ser. No. 08/644,694 (Attorney Docket No. TH0306), originally filed this same date, having the title Restructured Iron Oxide by S. N. Milam and B. H. Shanks. This patent application Ser. No. 08/356,024, now Ser. No. 08/644,694 is incorporated herein by reference.

Iron oxide compositions are predoped by heating them in the presence of another material which induces enhanced catalytic effect. Such materials include substances having one or more elements selected from the group consisting of Be, Mg, Ca, Sr, Ba, Sc, Ti, Zr, Hf, V, Ta, Mo, W, Mn, Tc, Re, Ru, Os, Co, Rh, Ir, Ni, Pd, Pt, Cu, Ag, Au, Zn, Cd, Hg, Al, Ga, In, Tl, Ge, Sn, Pb, Bi, Ce, Pr, Nd, Pm, Sm, Eu, Gd, Tb, Dy, Ho, Er, Tm, Yb, and Lu. Such substances can include, for example monometallic oxidic salts such as ammonium dimolybdate; bimetallic oxidic salts such as potassium permanganate; simple salts such as carbonates (eg., cerium (III) carbonate), nitrates (eg., magnesium nitrate), and hydroxides; oxides such as copper oxide; carbon containing compounds such as calcium acetate; mixtures thereof and hydrates or solvates thereof. Preferred compounds for this purpose are comprised of molybdenum, copper, calcium, zinc, cobalt, and cerium. The most preferred compounds for this purpose are ammonium dimolybdate, molybdenum trioxide, copper oxide, zinc oxide, calcium acetate, cobalt carbonate, and cerium (III) carbonate.

Thus far, it has been found that between about 0.5% wt and 6% wt (based on total weight of the predopant and iron oxide mixture) of these materials are useful in predoping the iron oxide. However, the specific amount of materials used to predope the iron oxide is not perceived to be critical to the invention. Not wishing to be bound to theory, it is believed that predoping the iron oxide is itself a catalytic process. That is, the material used to predope the iron oxide reduces the energy of activation for a physical alteration of the iron oxide which physical change is manifested in enhanced catalytic performance when the iron oxide is then used in a catalyst formulation (one parameter of which may be the enlargement of median pore diameter as set forth below). Thus, greater or lesser quantities of agents used to predope the iron oxide other than those mentioned above will also enhance the catalytic performance of the iron oxide based catalysts albeit, perhaps, to a variable degree.

This process requires the mixture of the iron oxide and the material used to predope it to be heated to a temperature of at least about 600° C. However, the temperature cannot exceed about 1600° C., the melting point of iron oxide. The application of this heat over time periods between about 10 minutes and 3 hours has been found to be effective. Again, while not being bound to theory, it is believed that the iron oxide mixed with predoping material must be subjected to this heat for a time sufficient to cause the iron oxide to undergoe its change in physical structure. In any event, it is most preferred that the iron oxide and predopant mixture is maintained at this elevated temperature for at least about 20 minutes to one hour.

Mass transfer within the pore structure or the interparticulate void space of a catalyst is important to the efficacy and efficiency of the catalyst system. The distribution and form of space or pores about and within the particles has much to do with the mass transfer associated with catalysis. Surface area, median pore diameter and pore volume are measurements associated with these aspects of the particles. Throughout this specification, surface area of the catalyst is determined by the well known B.E.T. method. The median pore diameter and pore volume will be used to represent the measurements taken by the method of mercury instrusion porosimetry.

Preferred predoped iron oxide particles made according to this invention and used in the catalysts and process of this invention display surface areas less than about 1.9 meters squared per gram ($m^2/g$) as measured by the B.E.T. method. Median pore diameters of the catalysts made from these predoped iron oxides range from between about 2500 Å to about 15,000 Å as measured by mercury intrusion porosimetry. Effective predoping of the iron oxide is also accompanied by a decrease of between about 5 and 75% in the pore volume of the catalyst made therefrom with respect to an analagous catalyst made with non-predoped iron oxide. Preferred catalysts show a decrease in pore volume of between about 20 and 75%. Most preferred catalysts show a decrease in pore volume of between about 30 and 75%.

Catalyst forms such as pellets, tablets, spheres, pills, saddles, trilobes, tetralobes and the like are formed from the predoped iron oxide of this invention. The iron oxide is mixed with predopant before it is heated and before the catalyst is prepared into a form such as a pellet. Moreover, in some embodiments of this invention, the iron oxide is mixed with a predopant, heated and cooled and then further mixed with additives and/or promoters. This mixture or blend is then molded into the various forms mentioned above (or others) and then heated and cooled again.

Dehydrogenation processes using the catalysts of this invention are carried out using a molar ratio of steam to compound of Formula II in the range of from about 2 to about 20. Preferably, the range is from about 5 to about 13. Reaction temperatures are in a range of from about 400 to about 750° C. Preferably, the range is from about 550 to about 650° C. The process may be carried out at atmospheric, superatmoshperic, or sub-atmoshperic pressures. Atmospheric or sub-atmospheric pressures are preferred. Liquid Hourly Space Velocities (LHSV) range from between about 0.1 and about 5 l/l/hour, using, for example, a tubular or radial flow reactor.

The term "selectivity" as used herein is defined as the amount of compound of Formula II that has been converted into compound of Formula I divided by the total amount of compound of Formula II that has been converted to any product times one hundred. In this specification selectivities are typically measured at a standard conversion level for compound of formula II. For example, as used herein $S_{70}$ refers to the molar selectivity of ethylbenzene conversion to styrene at 70% molar conversion of ethylbenzene. The activity of a catalyst is inversely related to the temperature. The more active the catalyst, the lower is the temperature that will be needed to obtain the same degree of conversion. Activities utilized in the instant specification are typically related to a given degree of conversion. For example, $T_{70}$ refers to the temperature at which a 70% molar conversion of ethylbenzene to any product occurs.

EXAMPLES

In each example that is not a comparative example, an iron oxide composition was first predoped by mixing iron oxide with various dry components (for about 10 minutes in a mixer-muller except as otherwise noted), adding deionized water or dilute aqueous $H_2SO_4$ and continuing mixing (for 5–15 minutes for a total mixing time of 25 minutes except as otherwise noted). The mixed components were then screened through a standard No. 7 sieve to break up any lumps, placed in dishes, and loaded into a muffle furnace at 170° C. These mixtures were then heated to the temperature indicated in the examples by ramping the furnace temperature at 6° C. per minute. The temperatures were maintained at the set point for one hour. Thereafter, the furnace was turned off and the iron oxide powder, treated as above, was allowed to cool to room temperature, in the furnace, over night (except as otherwise noted).

The iron oxide used in the comparative examples are the base cases for the examples according to the invention. That is, the iron oxide of the comparative examples have not been predoped according to this invention. The iron oxide catalyst examples according to this invention were prepared by predoping the iron oxide of the comparative examples with the materials listed in the examples at the conditions specified. Thus, Comparative Example A is the base case (non-predoped) for Examples 1–12; Comparative Example B is the base case (non-predoped) for Examples 13–14; Comparative Example C is the base case (non-predoped) for Example 15; Comparative Example D is the base case (non-predoped) for Examples 16–17; and Comparative Example E is the base case (non-predoped) for Example 18. Comparative Example F is the base case (non-predoped) for Comparative Example F1 (non-predoped) which is without corresponding examples according to this invention.

To test the catalytic effect of predoped iron oxide, each mixture formed as outlined above and each iron oxide comparative example sample was then formed into ⅛ inch catalyst pellets. This was done by taking the iron oxide composition and mixing it with various ingredients for about 10 minutes in a mixer-muller except as otherwise noted, adding deionized water and continuing mixing (for 5–15 minutes for a total mixing time of 25 minutes except as otherwise noted). The mixed components were then screened through a standard No. 7 sieve to break up any lumps and then processed through a laboratory scale California Pellet Mill. The pellets so obtained were then dried for about 15–60 minutes at 170° C. in an electrically heated drying oven and then transferred to an electrically heated muffle furnace where they were calcined at 800–825° C. for about one hour.

The catalyst pellets were then used in the preparation of styrene from ethylbenzene under isothermal conditions in a reactor designed for continuous operation. The conditions of the catalyst test were as follows: 100 cm$^3$ of catalyst, 600° C. reactor temperature, LHSV of 0.65 measured in liters of ethylbenzene per liter of catalyst per hour, a steam to ethylbenzene molar ratio of 10: 1, and a reactor pressure of 0.75 atmospheres.

The catalyst testing results are reported in terms of $T_{70}$ and $S_{70}$ where $T_{70}$ is the temperature required for a given catalyst to convert 70% of the ethylbenzene feed to products and $S_{70}$ is the molar selectivity to product styrene.

Catalytic performance data for catalysts made from non-predoped iron oxides and the predoped iron oxide of the examples are summarized in Table 1 below.

EXAMPLE A (COMPARATIVE)

Synthetic Red Iron Oxide

An iron oxide catalyst was prepared by adding 18.6 grams of calcium carbonate, 126.0 grams of cerium (III) carbonate, 25.8 grams of ammonium dimolybdate, and 255.1 grams of potassium carbonate, to 1103.5 grams of branched acicular synthetic red iron oxide; 201.3 grams of deionized water was added in the mixing step.

EXAMPLE 1-A

Red Iron Oxide Predoped with Ammonium Dimolybdate

An iron oxide composition was formed by predoping 1204 grams of branched acicular synthetic red iron oxide with 28.1 grams of ammonium dimolybdate in the process noted above; 220 grams of deionized water was added during the mixing step and the mixture was ultimately heated to 750° C.

Catalyst ingredients included 18.6 grams of calcium carbonate, 126.0 grams of cerium (III) carbonate, 255.1 grams of potassium carbonate, and 1121.8 grams of pre-doped iron oxide; 106.8 grams of deionized water was added during the mixing step of catalyst preparation.

EXAMPLE 1

Red Iron Oxide Predoped with Ammonium Dimolybdate

An iron oxide composition was formed by predoping 1204 grams of branched acicular synthetic red iron oxide with 28.1 grams of ammonium dimolybdate in the process noted above; 220 grams of deionized water was added to the mixture during the mixing step and the mixture was ultimately heated to 825° C.

Catalyst ingredients included 18.6 grams of calcium carbonate, 126.0 grams of cerium (III) carbonate, 255.1 grams of potassium carbonate, and 1121.8 grams of pre-doped iron oxide; 82.2 grams of deionized water was added during the mixing step of catalyst preparation.

EXAMPLE 1-C

Red Iron Oxide Predoped with Ammonium Dimolybdate

An iron oxide composition was formed by predoping 1204 grams of branched acicular synthetic red iron oxide with 28.1 grams of ammonium dimolybdate in the process noted above; 220 grams of deionized water was added to the mixture during the mixing step and the mixture was ultimately heated to 900° C.

Catalyst ingredients included 19.0 grams of calcium carbonate, 128.5 grams of cerium (III) carbonate, 260.2 grams of potassium carbonate, and 1143.6 grams of pre-doped iron oxide; 63.7 grams of deionized water was added during the mixing step of catalyst preparation.

EXAMPLE 1-D

Red Iron Oxide Predoped with Ammonium Dimolybdate

An iron oxide composition was formed by predoping 1500 grams of branched acicular synthetic red iron oxide with 35.1 grams of ammonium dimolybdate in the process noted above; 250 grams of deionized water was added during the mixing step and the mixture was ultimately heated to 950° C.

Catalyst ingredients included 18.6 grams of calcium carbonate, 126.0 grams of cerium (III) carbonate, 255.1 grams of potassium carbonate, and 1121.8 grams of pre-doped iron oxide; 54.8 grams of deionized water was added to the mixture during the mixing step of catalyst preparation.

EXAMPLE 2-A

Red Iron Oxide Predoped with Copper (II) Oxide

An iron oxide composition was formed by predoping 1208.0 grams of branched acicular synthetic red iron oxide with 9.7 grams of copper oxide in the process noted above; 110 grams of deionized water was added to the mixture during the mixing step and the mixture was heated to 975° C. by inserting it into the furnace preheated to 975° C. The predoped iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1108.9 grams of predoped iron oxide; 89.6 grams of deionized water was added to the mixture during the mixing step of catalyst preparation.

EXAMPLE 2-B

Red Iron Oxide Predoped with Copper (II) Oxide

An iron oxide composition was formed by predoping 1208.0 grams of branched acicular synthetic red iron oxide with 19.4 grams of copper oxide in the process noted above; 110 grams of deionized water was added to the mixture during the mixing step and the mixture was heated to 975° C. by inserting it into the furnace preheated to 975° C. The predoped iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1117.8 grams of predoped iron oxide; 100.1 grams of deionized water was added to the mixture during the mixing step of catalyst preparation.

EXAMPLE 2-C

Red Iron Oxide Predoped with Copper (II) Oxide

An iron oxide composition was prepared by predoping 1208.0 grams of branched acicular synthetic red iron oxide with 29.1 grams of copper oxide in the process noted above; 110 grams of deionized water was added to the mixture during the mixing step and the mixture was heated to 975° C. by inserting it into the furnace preheated to 975° C. The predoped iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1126.6 grams of predoped iron oxide; 87.2 grams of deionized water was added to the mixture during the mixing step of catalyst preparation.

EXAMPLE 2-D

Red Iron Oxide Predoped with Copper (11) Oxide

An iron oxide composition was prepared by predoping 1208.0 grams of branched acicular synthetic red iron oxide with 48.4 grams of copper oxide in the process noted above; 110 grams of deionized water was added to the mixture during the mixing step and the mixture was heated to 975° C. by inserting it into the furnace preheated to 975° C. The predoped iron oxide composition was removed from the furnace after one hour and was cooled by exposure to ambient room conditions (about 20° C.).

Catalyst ingredients included 18.6 grams of calcium carbonate, 126.9 grams of cerium (III) carbonate, 25.8 grams of ammonium dimolybdate, 255.3 grams of potassium carbonate, and 1144.4 grams of predoped iron oxide; 113.5 grams of deionized water was added to the mixture during the mixing step of catalyst preparation.

EXAMPLE 3

Red Iron Oxide Predoped with Calcium (II) Acetate

An iron oxide composition was prepared by predoping 1200.0 grams of branched acicular synthetic red iron oxide with 32.0 grams of calcium acetate dissolved in 150 grams of deionized water, over 15 minutes, while mulling (mixing). The mixture was placed in stainless steel dishes, dried in an electrically heated drying oven, 30 minutes at 170° C., and then was and loaded into an electrically heated muffle furnace at 700° C. Air flow through the furnace was maintained at 40 scf/hr throughout the calcination. The furnace temperature was ramped to 900° C., over one hour, and was maintained at that set point temperature for one hour. Thereafter, the furnace was turned off and the iron oxide powder, treated as above, was allowed to cool to room temperature, over night.

Catalyst ingredients included 121.3 grams of cerium (III) carbonate, 25.6 grams of ammonium dimolybdate, 245.6 grams of potassium carbonate, and 1110.4 grams of predoped iron oxide; 92.3 grams of deionized water was added to the mixture during the mixing step of catalyst preparation.

EXAMPLE 4

Red Iron Oxide Predoped with Zinc (II) Oxide

An iron oxide compositions was prepared by predoping 1200.0 grams of branched acicular synthetic red iron oxide with 19.9 grams of zinc oxide in the process noted above; 220 grams of deionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1118.2 grams of predoped iron oxide; 125.0 grams of deionized water was added to the mixture during the mixing step of catalyst preparation.

EXAMPLE 5

Red Iron Oxide Predoped with Tin (IV) Oxide

An iron oxide composition was prepared by predoping 1200.0 grams of branched acicular synthetic red iron oxide with 36.7 grams of tin oxide in the process noted above; 220 grams of deionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1133.6 grams of predoped iron oxide; 146.5 grams of deionized water was added to the mixture during the mixing step of catalyst preparation.

EXAMPLE 6

Red Iron Oxide Predoped with Manganese (IV) Oxide

An iron oxide composition was prepared by predoping 1200.0 grams of branched acicular synthetic red iron oxide with 21.2 grams of manganese oxide in the process noted above; 220 grams of deionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1119.4 grams of predoped iron oxide; 116.8 grams of deionized water was added to the mixture during the mixing step of catalyst preparation.

EXAMPLE 7

Red Iron Oxide Predoped with Vanadium (V) Oxide

An iron oxide composition was prepared by predoping 1203.0 grams of branched acicular synthetic red iron oxide with 22.1 grams of vanadium oxide in the process noted above; 220 grams of deionized water was added to the mixture during the mixing step and the mixture was ultimately heated to a temperature of 700° C.

Catalyst ingredients included 18.6 grams of calcium carbonate, 126.0 grams of cerium (III) carbonate, 25.8 grams of ammonium dimolybdate, 255.1 grams of potassium carbonate, and 1120.3 grams of predoped iron oxide; 154.0 grams of deionized water was added to the mixture during the mixing step of catalyst preparation.

EXAMPLE 8

Red Iron Oxide Predoped with Titanium (IV) Oxide

An iron oxide composition was prepared by predoping 1200.0 grams of branched acicular synthetic red iron oxide with 19.4 grams of titanium oxide in the process noted above; 220 grams of deionized water was added to the mixture during the mixing step and the mixture was ultimately heated to 975° C.

Catalyst ingredients included 18.6 grams of calcium carbonate, 126.0 grams of cerium (III) carbonate, 25.8 grams of ammonium dimolybdate, 255.1 grams of potassium carbonate, and 1117.8 grams of predoped iron oxide; 115.0 grams of deionized water was added to the mixture during the mixing step of catalyst preparation.

EXAMPLE 9

Red Iron Oxide Predoped with Bismuth (III) Oxide

An iron oxide composition was prepared by predoping 1200.0 grams of branched acicular synthetic red iron oxide with 56.7 grams of bismuth oxide in the process noted above; 220 grams of deionized water was added to the mixture during the mixing step and the mixture was ultimately heated to 825° C.

Catalyst ingredients included 18.6 grams of calcium carbonate, 126.0 grams of cerium (III) carbonate, 25.8 grams of ammonium dimolybdate, 255.1 grams of potassium carbonate, and 1152.0 grams of predoped iron oxide; 136.3 grams of deionized water was added to the mixture during the mixing step of catalyst preparation.

EXAMPLE 10

Red Iron Oxide Predoped with Lead (II) Oxide

An iron oxide composition was prepared by predoping 1200.0 grams of branched acicular synthetic red iron oxide with 54.3 grams of lead oxide in the process outlined above; 220 grams of deionized water was added to the mixture during the mixing step and the mixture was ultimately heated to 900° C.

Catalyst ingredients included 18.6 grams of calcium carbonate, 126.0 grams of cerium (III) carbonate, 25.8 grams of ammonium dimolybdate, 255.1 grams of potassium carbonate, and 1149.8 grams of predoped iron oxide; 114.0 grams of deionized water was added to the mixture during the mixing step of catalyst preparation.

EXAMPLE 11

Red Iron Oxide Predoped with Cobalt (II) Carbonate

An iron oxide composition was prepared by predoping 1204.0 grams of branched acicular synthetic red iron oxide with 29.0 grams of cobalt carbonate in the process noted above; 220 grams of deionized water was added to the mixture during the mixing step and the mixture was ultimately heated to 975° C.

Catalyst ingredients included 18.6 grams of calcium carbonate, 126.9 grams of cerium (III) carbonate, 25.8 grams of ammonium dimolybdate, 255.3 grams of potassium carbonate, and 1116.7 grams of predoped iron oxide; 125.0 grams of deionized water was added to the mixture during the mixing step of catalyst preparation.

EXAMPLE 12

Red Iron Oxide Predoped with Cerium (III) Carbonate

An iron oxide composition was prepared by predoping 1204.0 grams of branched acicular synthetic red iron oxide with 68.0 grams of cerium (III) carbonate in the process noted above; 220 grams of deionized water was added to the mixture during the mixing step and the mixture was ultimately heated to 975° C.

Catalyst ingredients included 18.6 grams of calcium carbonate, 126.9 grams of cerium (III) carbonate, 25.8 grams of ammonium dimolybdate, 255.3 grams of potassium carbonate, and 1138.4 grams of predoped iron oxide; 142.0 grams of deionized water was added to the mixture during the mixing step of catalyst preparation.

EXAMPLE B (COMPARATIVE)

Catalyst Prepared with Synthetic Red Iron Oxide

An iron oxide catalyst was prepared by adding 20.1 grams of calcium carbonate, 103.1 grams of cerium (III) carbonate, 32.3 grams of ammonium paratungstate, and 200.9 grams of potassium carbonate, to 902.9 grams of branched acicular synthetic red iron oxide; 119.1 grams of deionized water was added to the mixture during the mixing step.

EXAMPLE 13

Red Iron Oxide Predoped with Ammonium Paratungstate

An iron oxide composition was prepared by predoping 1500 grams of branched acicular synthetic red iron oxide with 53.8 grams of ammonium paratungstate in the process noted above; 250 grams of deionized water was added to the mixture during the mixing step and the mixture was ultimately heated to 950° C.

Catalyst ingredients included 24.8 grams of calcium carbonate, 126.0 grams of cerium (III) carbonate, 255.6 grams of potassium carbonate, and 1135.2 grams of predoped iron oxide; 81.4 grams of deionized water was added to the mixture during the mixing step of catalyst preparation.

EXAMPLE 14

Red Iron Oxide Predoped with Tungsten (VI) Oxide

An iron oxide composition was prepared by predoping 1500 grams of branched acicular synthetic red iron oxide with 47.9 grams of tungsten oxide in the process noted above; 250 grams of deionized water was added to the mixture during the mixing step and the mixture was ultimately heated to 950° C.

Catalyst ingredients included 24.8 grams of calcium carbonate, 126.0 grams of cerium (III) carbonate, 255.6 grams of potassium carbonate, and 1135.2 grams of predoped iron oxide; 81.4 grams of deionized water was added to the mixture during the mixing step of catalyst preparation.

EXAMPLE C (COMPARATIVE)

Catalyst Prepared with Synthetic Red Iron Oxide

A catalyst was prepared by adding 18.5 grams of calcium carbonate, 119.8 grams of cerium (III) carbonate, 25.6 grams of ammonium dimolybdate, and 245.6 grams of potassium carbonate, to 1103.2 grams of random spheroidal synthetic red iron oxide; 157.2 grams of deionized water was added to the mixture during the mixing step.

EXAMPLE 15

Red Iron Oxide Predoped with Molybdenum (VI) Oxide

An iron oxide composition was prepared by predoping 1200 grams of random spheroidal synthetic red iron oxide with 47.7 grams of molybdenum trioxide according the process noted above; 220 grams of deionized water was added to the mixture during the mixing step and the mixture was ultimately heated to 825° C.

Catalyst ingredients included 17.7 grams of calcium carbonate, 115.7 grams of cerium (III) carbonate, 242.5 grams of potassium carbonate, and 1086.4 grams of pre-doped iron oxide; 94.8 grams of deionized water was added to the mixture during the mixing step of catalyst preparation.

EXAMPLE D (COMPARATIVE)

Catalyst Prepared with Synthetic Red Iron Oxide

A catalyst was prepared by adding 20.3 grams of calcium carbonate, 103.1 grams of cerium (III) carbonate, 32.3 grams of ammonium paratungstate, and 200.9 grams of potassium carbonate, to 900.0 grams of random spheroidal synthetic red iron oxide; 124.6 grams of deionized water was added to the mixture during the mixing step.

EXAMPLE 16

Red Iron Oxide Predoped with Magnesium (II) Nitrate

An iron oxide composition was prepared by predoping 1200 grams of random spheroidal synthetic red iron oxide with 69.4 grams of magnesium nitrate dissolved in 100 grams of deionized water, over 15 minutes, while mulling (mixing). The mixture was placed in ceramic dishes and then was loaded into an electrically heated muffle furnace at 170° C. and dried for 30 minutes. The furnace temperature was then ramped, at 6° C./min. from 170 to 950° C., and was maintained at 950° C. for one hour. Air flow through the furnace was maintained at 40 scf/hr throughout the calcination. Thereafter, the furnace was turned off and the iron oxide powder, treated as above, was allowed to cool to room temperature, in the furnace, over night.

Catalyst ingredients included 20.3 grams of calcium carbonate, 102.8 grams of cerium (III) carbonate, 32.1 grams of ammonium paratungstate, 200.8 grams of potassium carbonate, and 908.2 grams of predoped iron oxide; 80.2 grams of deionized water was added to the mixture during the mixing step of catalyst preparation.

EXAMPLE 17

Red Iron Oxide Predoped with Potassium Permanganate

An iron oxide composition was prepared by predoping 1200 grams of random spheroidal synthetic red iron oxide with 10.0 grams of potassium permanganate dissolved in 250 grams of deionized water, over 15 minutes, while mulling (mixing). The mixture was screened through a standard No. 7 sieve to break up any lumps and then was placed in ceramic dishes and loaded into an electrically heated muffle furnace at 170° C. The furnace temperature was then ramped at 6° C./min. to 950° C. and was maintained at the set point temperature for one hour. Thereafter, the furnace was turned off and the iron oxide powder, treated as above, was allowed to cool to room temperature, in the furnace, over night.

Catalyst ingredients included 22.5 grams of calcium carbonate, 114.5 grams of cerium (III) carbonate, 35.8 grams of ammonium paratungstate, 232.4 grams of potassium carbonate, and 1000.0 grams of predoped iron oxide; 118.0 grams of deionized water was added to the mixture during the mixing step of catalyst preparation.

EXAMPLE E (COMPARATIVE)

Catalyst Prepared with Synthetic Yellow Iron Oxide

A catalyst was prepared by adding 18.6 grams of calcium carbonate, 126.0 grams of cerium (III) carbonate, 25.8 grams of ammonium dimolybdate, and 255.3 grams of potassium carbonate, to 1290.9 grams of branched acicular synthetic yellow iron oxide; 214.2 grams of deionized water was added to the mixture during the mixing step.

EXAMPLE 18

Yellow Iron Oxide Predoped with Molybdenum (VI) Oxide

An iron oxide composition was prepared by predoping 1408.3 grams of branched acicular synthetic yellow iron oxide with 47.6 grams of molybdenum oxide in the process noted above; 220 grams of deionized water was added to the mixture during the mixing step and the mixture was ultimately heated to 800° C.

Catalyst ingredients included 18.6 grams of calcium carbonate, 126.0 grams of cerium (III) carbonate, 255.3 grams of potassium carbonate, and 1143.6 grams of pre-doped iron oxide; 91.7 grams of deionized water was added to the mixture during the mixing step of catalyst preparation.

EXAMPLE F (COMPARATIVE)

Synthetic Red Iron Oxide

Catalyst ingredients included 18.5 grams of calcium carbonate, 119.8 grams of cerium (III) carbonate, 25.6 grams of ammonium dimolybdate, 245.6 grams of potassium carbonate, and 1103.6 grams of branched acicular synthetic red iron oxide; 157.2 grams of deionized water was added to the mixture during the mixing step of catalyst preparation.

EXAMPLE F1 (COMPARATIVE)

Heated Synthetic Red Iron Oxide

An iron oxide composition was prepared by heating 1400 grams of branched acicular synthetic red iron oxide. The iron oxide was placed in stainless steel dishes and loaded into an electrically heated muffle furnace at 600° C. Air flow through the furnace was maintained at 40 scf/hr throughout the calcination. The furnace temperature was ramped at 6° C./min. to 900° C., and was maintained at that set point temperature for one hour. Thereafter, the furnace was turned off and the iron oxide powder, treated as above, was allowed to cool to room temperature, over night.

Catalyst ingredients included 18.6 grams of calcium carbonate, 119.8 grams of cerium (III) carbonate, 25.6 grams of ammonium dimolybdate, 245.6 grams of potassium carbonate, and 1100.0 grams of heated iron oxide; 125.0 grams of deionized water was added to the mixture during the mixing step of catalyst preparation.

TABLE 1

Catalyst Physical Properties and Performance Results

| Example | Catalyst Median Pore Diameter, Angstroms | Catalyst Pore Volume, cm³/g | $T_{70}$ | $S_{70}$ |
|---|---|---|---|---|
| Comp. Ex. A | 2,743 | 0.1941 | 595 | 94.4 |
| 1-A | 2,281 | 0.1271 | 596 | 95.0 |
| 1-B | 6,654 | 0.0979 | 596 | 96.0 |
| 1-C | 9,524 | 0.0707 | 600 | 96.4 |
| 1-D | 14,816 | 0.1024 | 609 | 96.4 |
| 2-A | 6,255 | 0.1324 | 596 | 95.7 |
| 2-B | 5,459 | 0.145 | 598 | 95.3 |
| 2-C | 4,898 | 0.1348 | 595 | 95.0 |
| 2-D | 5,679 | 0.1421 | 594 | 94.0 |
| 3 | 3,830 | 0.112 | 590 | 96.0 |
| 4 | 4,871 | 0.1471 | 598 | 95.6 |
| 5 | 4,334 | 0.1482 | 602 | 95.1 |
| 6 | 4,403 | 0.1243 | 597 | 95.3 |
| 7 | 2,929 | 0.1587 | 611 | 95.3 |
| 8 | 4,915 | 0.1335 | 599 | 95.2 |
| 9 | 7,158 | 0.1256 | 602 | 95.7 |
| 10 | 2,351 | 0.1229 | 601 | 94.9 |
| 11 | 5,057 | 0.1408 | 598 | 95.6 |
| 12 | 4,698 | 0.1462 | 594 | 95.3 |
| Comp. Ex. B | 2,519 | 0.1688 | 603 | 95.0 |
| 13 | 5,111 | 0.0895 | 606 | 95.9 |
| 14 | 4,229 | 0.0931 | 605 | 95.8 |
| Comp. Ex. C | 3,625 | 0.1679 | 594 | 95.7 |
| 15 | 6,994 | 0.1153 | 597 | 96.4 |
| Comp. Ex. D | 3,164 | 0.1704 | 599 | 95.5 |
| 16 | 5,079 | 0.1561 | 600 | 95.8 |
| 17 | 5,020 | 0.1476 | 599 | 95.9 |
| Comp. Ex. E | 1,440 | 0.1644 | 591 | 93.3 |
| 18 | 3,630 | 0.1068 | 599 | 96.0 |
| Comp. Ex. F | 2,720 | 0.160 | 593 | 95.4 |
| Comp. Ex. F1 | 3,696 | 0.1238 | 591 | 95.4 |

This data shows the improved catalyst selectivity attained by predoping the iron oxide. Selectivity gains were attained with little or no corresponding loss in catalyst activity and corresponded to an increase in the catalyst median pore diameter and/or a decrease in catalyst pore volume. Comparative Examples F and F1 show that simply heating iron oxide before catalyst preparation does not result in increased catalyst selectivity.

What is claimed is:

1. In a process for dehydrogenation of an organic composition having a saturated portion comprising contacting said composition having said saturated portion with a catalytic quantity of an iron (III) oxide catalyst the improvement consisting of employing as said catalyst, iron (III) oxide predoped by being heated to a temperature between 600° C. and 1600° C. in the presence of between about 0.5% wt and 6% wt of a substance comprising a member of the group consisting of Be, Mg, Ca, Sr, Ba, Sc, Ti, Zr, Hf, V, Ta, Mo, W, Mn, Tc, Re, Ru, Os, Co, Rh, Ir, Ni, Pd, Pt, Cu, Ag, Au, Zn, Cd, Hg, Al, Ga, In, Ti, Ge, Sn, Pb, Bi, Ce, Pr, Nd, Pm, Sm, Eu, Gd, Tb, Dy, Ho, Er, Tm, Yb, and Lu (based on the total weight of the substance with which the iron (III) oxide is predoped and the iron (III) oxide), wherein the predoped iron oxide has then been cooled the cooled predoped iron oxide is additionally mixed with promoters to form a mixture which is formed into a shaped catalyst form, and then calcined.

2. The process of claim 1 wherein ethylbenzene is dehydrogenated to form styrene.

3. The process of claim 1 wherein said predoping substance is a compound comprising an element selected from the group consisting of molybdenum, copper, calcium, zinc, cobalt, and cerium.

4. The process of claim 3 wherein said compound is selected from the group consisting of ammonium dimolybdate, molybdenum trioxide, copper oxide, zinc oxide, calcium acetate, cobalt carbonate, and cerium (II) carbonate.

5. The process of claim 1 wherein said iron oxide catalyst exhibits a pore volume between about 0.05 and 0.18 cm³/gram.

6. The process of claim 1 wherein said iron oxide catalyst exhibits a pore volume between about 0.05 and 0.15 cm³/gram.

7. The process of claim 6 wherein said iron oxide catalyst exhibits a pore volume between about 0.05 and 0.13 cm³/gram.

8. The process of claim 1 wherein said iron oxide is cooled after predoping and then additionally mixed with K and one or more promoters comprising a member of the group consisting of Sc, Y, La, rare earths, Mo, W, Ca, Mg, V, Cr, Co, Ni, Mn, Cu, Zn, Cd, Al, Sn, Bi, and mixtures thereof prior to extrudate formation.

9. The process of claim 8 used to convert ethylbenzene to styrene.

* * * * *